(12) United States Patent
Chanduszko

(10) Patent No.: US 12,090,073 B2
(45) Date of Patent: *Sep. 17, 2024

(54) SHORT STENT

(71) Applicant: C. R. Bard, Inc., Franklin Lakes, NJ (US)

(72) Inventor: Andrzej J. Chanduszko, Chandler, AZ (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 313 days.

This patent is subject to a terminal disclaimer.

(21) Appl. No.: 17/153,723

(22) Filed: Jan. 20, 2021

(65) Prior Publication Data

US 2021/0161693 A1 Jun. 3, 2021

Related U.S. Application Data

(62) Division of application No. 15/423,391, filed on Feb. 2, 2017, now Pat. No. 10,905,578.

(51) Int. Cl.
*A61F 2/966* (2013.01)
*A61F 2/915* (2013.01)
*A61F 2/958* (2013.01)

(52) U.S. Cl.
CPC .............. *A61F 2/966* (2013.01); *A61F 2/915* (2013.01); *A61F 2/958* (2013.01);
(Continued)

(58) Field of Classification Search
CPC ........ A61F 2/9522; A61F 2/966; A61F 2/962; A61F 2002/91583; A61F 2002/9505;
(Continued)

(56) References Cited

U.S. PATENT DOCUMENTS 5,091,205 A 2/1992 Fan
5,695,516 A 12/1997 Fischell et al.
(Continued)

OTHER PUBLICATIONS

U.S. Appl. No. 15/423,391, filed Feb. 2, 2017 Advisory Action dated Aug. 29, 2019.
(Continued)

*Primary Examiner* — Darwin P Erezo
*Assistant Examiner* — Christina C Lauer
(74) *Attorney, Agent, or Firm* — Rutan & Tucker LLP

(57) ABSTRACT

A stent delivery system includes an inner tubular member, a stent disposed over a distal section of the inner tubular member, a locking member positioned over the inner tubular member proximal of the stent, and an outer tubular member covering the stent and the locking member in a delivery configuration. A portion of the stent can be positioned in the locking member in the delivery configuration. The locking member can include a tubular proximal section, and a plurality of fingers extending distally from the tubular proximal section. The plurality of fingers can include a first finger and a second finger. The plurality of fingers can have a locked configuration with each of the first finger and the second finger parallel to a longitudinal axis, and an unlocked configuration with one of the first finger and/or the second finger forming an angle with respect to the longitudinal axis.

14 Claims, 8 Drawing Sheets

(52) U.S. Cl.
CPC ............... *A61F 2002/9665* (2013.01); *A61F 2230/0008* (2013.01); *A61F 2230/001* (2013.01); *A61F 2230/0056* (2013.01); *A61F 2230/0058* (2013.01)

(58) Field of Classification Search
CPC ............ A61F 2/95; A61F 2/9525; A61F 2002/91516; A61F 2002/91525; A61F 2002/91591; A61F 2002/91508; A61F 2/915; A61F 2002/823; A61F 2002/825; A61F 2/82
See application file for complete search history.

(56) References Cited

U.S. PATENT DOCUMENTS

| | | | |
|---|---|---|---|
| 5,935,162 A | 8/1999 | Dang | |
| 6,013,091 A | 1/2000 | Ley et al. | |
| 6,077,297 A | 6/2000 | Robinson et al. | |
| 6,623,518 B2 | 9/2003 | Thompson et al. | |
| 6,776,791 B1 | 8/2004 | Stallings et al. | |
| 6,936,058 B2 | 8/2005 | Forde et al. | |
| 10,278,839 B2* | 5/2019 | Giasolli | A61F 2/915 |
| 10,905,578 B2* | 2/2021 | Chanduszko | A61F 2/966 |
| 2002/0049490 A1* | 4/2002 | Pollock | A61F 2/91 |
| | | | 623/1.15 |
| 2002/0055767 A1* | 5/2002 | Forde | A61F 2/962 |
| | | | 623/1.11 |
| 2002/0120322 A1* | 8/2002 | Thompson | A61F 2/91 |
| | | | 623/1.11 |
| 2002/0120323 A1 | 8/2002 | Thompson et al. | |
| 2003/0176914 A1* | 9/2003 | Rabkin | A61F 2/91 |
| | | | 623/1.15 |
| 2004/0186555 A1* | 9/2004 | Bonsignore | A61F 2/915 |
| | | | 623/1.31 |
| 2004/0204749 A1 | 10/2004 | Gunderson | |
| 2004/0236406 A1 | 11/2004 | Gregorich | |
| 2006/0004434 A1 | 1/2006 | Forde et al. | |
| 2008/0051876 A1* | 2/2008 | Ta | A61F 2/82 |
| | | | 623/1.42 |
| 2009/0216314 A1* | 8/2009 | Quadri | A61F 2/2418 |
| | | | 623/1.16 |
| 2012/0226346 A1* | 9/2012 | Boismier | A61F 2/915 |
| | | | 623/1.15 |
| 2015/0057743 A1 | 2/2015 | Ta et al. | |
| 2015/0297376 A1* | 10/2015 | Chanduszko | A61F 2/90 |
| | | | 623/1.16 |

OTHER PUBLICATIONS

U.S. Appl. No. 15/423,391, filed Feb. 2, 2017 Final Office Action dated Jun. 21, 2019.
U.S. Appl. No. 15/423,391, filed Feb. 2, 2017 Final Office Action dated May 7, 2020.
U.S. Appl. No. 15/423,391, filed Feb. 2, 2017 Non-Final Office Action dated Dec. 17, 2018.
U.S. Appl. No. 15/423,391, filed Feb. 2, 2017 Non-Final Office Action dated Oct. 9, 2019.
U.S. Appl. No. 15/423,391, filed Feb. 2, 2017 Notice of Allowance dated Sep. 16, 2020.

* cited by examiner

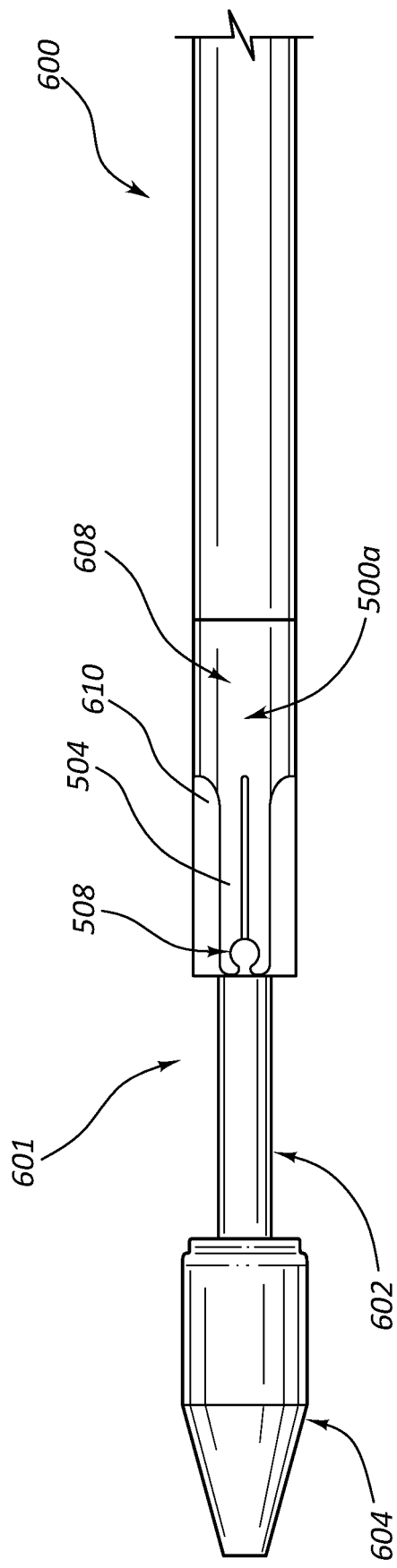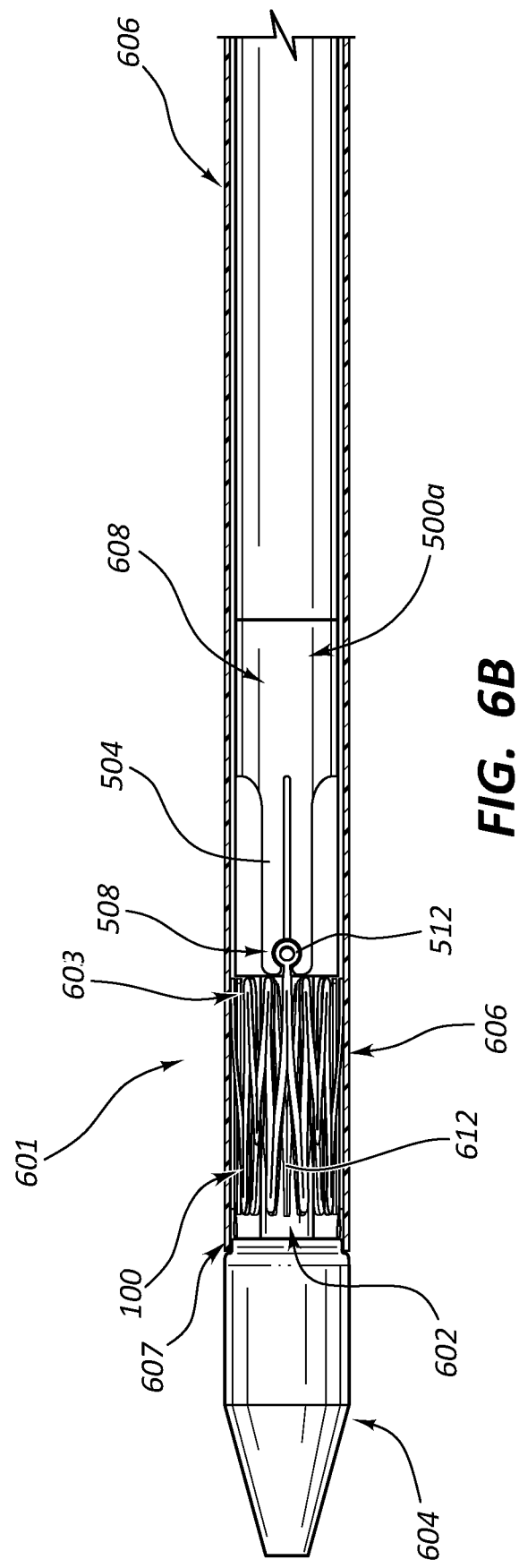
FIG. 6A
FIG. 6B

SHORT STENT

PRIORITY

This application is a division of U.S. patent application Ser. No. 15/423,391, filed Feb. 2, 2017, now U.S. Pat. No. 10,905,578, which is incorporated by reference into this application.

BACKGROUND

Intraluminal prostheses used to maintain, open, or dilate blood vessels are commonly known as stents. Stents have been used in various body lumens, including, e.g., the biliary tree, venous system, peripheral arteries, and coronary arteries. Stent generally include cylindrical frames that define a plurality of openings.

There are two broad classes of stents: self-expanding stents and balloon-expandable stents. Self-expanding stents expand intraluminally when a constraining cover is removed, such as a sheath of a stent delivery system. Other forms respond to elevated temperatures (due to the stent's material properties). Self-expanding stents are generally loaded into a delivery system by collapsing the stent from an expanded configuration at a first, larger diameter to a collapsed configuration at a second, smaller diameter. Balloon-expandable stents are typically characterized by intraluminal expansion using an inflation force, such as a balloon catheter. Balloon-expandable stents are generally loaded onto a balloon catheter using a crimping process to collapse the stent, and are plastically deformed when the balloon is inflated in the body vessel to the expanded configuration.

There are two basic architectures for stents, circumferential and helical. Circumferential architectures generally include a series of cylindrical rings, formed by a series of struts, connected by elements or bridges along a stent longitudinal axis. Helical configurations include a helical structure along the longitudinal axis of the stent, formed by a series of struts, connected by connecting elements or bridges.

Arterial and venous system stents can be made by machining a pattern of struts and connecting elements from a metal tube, typically by laser machining the pattern into the tube. The pattern of struts and connecting elements can be configured depending on the desired attributes, e.g. flexibility and bendability. The pattern can facilitate uniform expansion and curtail stent foreshortening upon expansion.

SUMMARY

Invention embodiments comprise a stent with butterfly-shaped cells and pinched-ellipsoid-shaped cells. In some embodiments, these cells contribute to a stent with a ring comprising two crown-shaped moieties having a multiplicity of vertexes disposed between struts and these moieties connect to each other crown bottom to crown bottom. In some embodiments, in addition to vertexes disposed between struts, the stents have a strut-vertex-bridge-vertex-strut sequence.

In these or other embodiments, the stent has a ring comprising first and second crown-shaped moieties having a multiplicity of vertexes wherein the vertexes are disposed between struts; one or more struts disposed between a crown-bottom vertex on the first ring and a crown-bottom vertex on the second ring; and one or more markers connected to a crown-top vertex. Sometimes these stents or the rings of these stents comprise a radiopaque insert disposed in the marker. And in some embodiments, the stent is adapted for balloon expansion.

In these or other embodiments, a stent comprises a first ring with two first moieties having a multiplicity of sections comprising a vertex disposed between struts; a first, type-I bridge disposed between the first moieties crown bottom to crown bottom; a second ring with two second moieties having a multiplicity of sections comprising a vertex disposed between struts; a second, type-I bridge disposed between the second moieties crown bottom to crown bottom; and a type-II bridge disposed between the rings crown top to crown top. In some embodiments, the stent had a sequence of struts, vertexes, and bridges of strut, vertex, type-I bridge, vertex, strut, vertex, type-II bridge, vertex, strut, vertex, type-I bridge, vertex, strut. In some embodiments, the first-ring struts and vertexes are arranged in a first butterfly-shaped cell and a first pinched-ellipsoid-shaped cell; and another ring has struts and vertexes arranged in a second butterfly-shaped cell and a second pinched-ellipsoid-shaped cell. Sometimes the first butterfly-shaped cell is different from the second butterfly-shaped cell and the first pinched-ellipsoid-shaped cell is different from the second pinched-ellipsoid-shaped cell. These embodiments can comprise markers, as well.

In these or other embodiments, a system comprising an inner catheter with a distal stent bed; and a stent disposed on the distal bed is disclosed. In some embodiments, the system also has a stent anchor disposed on the inner catheter proximal to the stent, in which the stent anchor comprises a receiver having a shape complementary to a stent component, such as a marker. Self-expanding or other versions of the system can have an outer sheath disposed over the stent and the stent anchor. Sometimes the stent anchor has one or more fingers and a finger or these fingers can contain a receiver or the receiver is disposed across fingers. In some embodiments, a finger is biased outward.

In these or other embodiments, the system has a stent with a compressed configuration and an expanded configuration and the diameter of the expanded configuration is greater than the diameter of the stent anchor. In some embodiments, the stent has struts, vertexes, and bridges in a sequence of strut, vertex, type-I bridge, vertex, strut, vertex, type-II bridge, vertex, strut, vertex, type-I bridge, vertex, strut. The system can have first-ring struts and vertexes that are arranged in a first butterfly-shaped cell and a first pinched-ellipsoid-shaped cell and second-ring struts and vertexes that are arranged in a second butterfly-shaped cell and a second pinched-ellipsoid-shaped cell. In some embodiments, the first butterfly-shaped cell is different from the second butterfly-shaped cell and the first pinched-ellipsoid-shaped cell is different from the second pinched-ellipsoid-shaped cell.

BRIEF DESCRIPTION OF FIGURES

FIG. 6A is a view of an embodiment of a delivery system containing a stent anchor and a stent bed.

FIG. 6B is a view of an embodiment of the delivery system of FIG. 6A also containing a crimped stent.

DETAILED DESCRIPTION

Figure 1A:
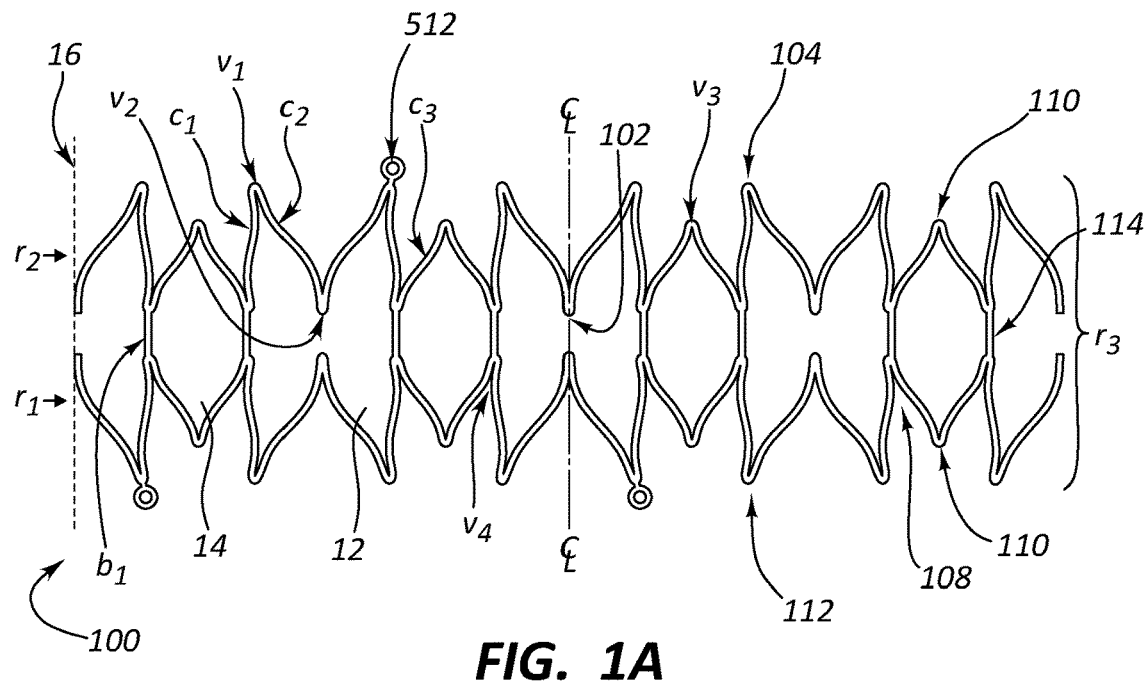
FIG. 1A is a stent embodiment shown in a laid-out configuration.

| | |
|---|---|
| stent cell A | 12 |
| stent cell B | 14 |
| stent cell C | 16 |
| stent cell D | 18 |
| stent | 100, 700 |
| vertex, v2 | 102 |
| vertex, v1 | 104 |
| vertex, v4 | 108 |
| vertex, v3 | 110 |
| bridge, b1, type-I | 114 |
| bridge, b2, type-II | 118 |
| curved strut, c2 | 120 |
| curved strut, c3 | 126 |
| curved strut, c1 | 130 |
| stent anchor | 500, 500a, 500b |
| finger | 504 |
| slit | 506 |
| receiver | 508 |
| marker | 512 |
| insert | 514 |
| stent delivery system | 600 |
| stent delivery system distal end | 601 |
| stent bed | 602 |
| proximal-most end of stent | 603 |
| distal tip | 604 |
| outer sheath | 606 |
| distal-most end of outer sheath | 607 |
| tube | 608 |
| inner catheter | 610 |
| stent | 700, 100 |

The following description and accompanying figures describe and show certain embodiments to demonstrate, in a non-limiting manner, several possible stent frame and stent holder configurations. The patterns can be incorporated into any intraluminal prosthesis, such as a self-expanding stent or a balloon-expandable stent, without limitation. In some embodiments, the disclosed pattern may be machined (e.g., laser machined) from a seamless metal or polymer tube. Non-limiting examples of metal tubes include stainless steel (e.g., AISI 316 SS), titanium, cobalt-chromium alloys, and nickel titanium alloys (nitinol). In other embodiments, the pattern may be formed into a metal or polymer sheet rolled into a tubular shape. The tubes or sheets may be heat-treated, annealed, or electropolished. Other known treatments are also contemplated.

The term "stent architecture" means the various stent features that contribute to its form, including the stent wall pattern. The term "stent cell" means a portion of the pattern that repeats along a circumferential or longitudinal path.

Extensive foreshortening, the stent getting shorter as it expands, can lead to inaccurate stent deployment. In certain embodiments, the stent architecture is designed to prevent excessive foreshortening. Other design considerations include in vivo stent flexibility and patency. Other designs minimize the profile of the collapsed stent. In certain embodiments, the stent architecture prevents excessive foreshortening.

Some of the drawings show stents in an expanded configuration, but laid-flat. These are but one possible configuration. Depending on the target vessel size, the stent can be over expanded, which could slightly alter the element's shape or their relationship to one another (e.g., elements parallel to the stent longitudinal axis may be oblique at over expanded diameters). Some drawings show the stents in an as-cut configuration and are top views of the stent. In some embodiments, the stents are formed in a tube having a diameter of about 4.8 mm. In some embodiments, the stents are formed in a tube having a diameter of about 6.4 mm. These are non-limiting tube diameter examples. In general, the tube diameters are based on target vessel diameters with larger tube diameters being selected for larger target vessels). Various stent embodiments have a longitudinal length, indicated as l in the figures, in the range from about 3 mm to about 20 mm or about 6 mm to about 12 mm, although longer lengths are also contemplated without limitation, depending on the particular application.

Figure 1B:
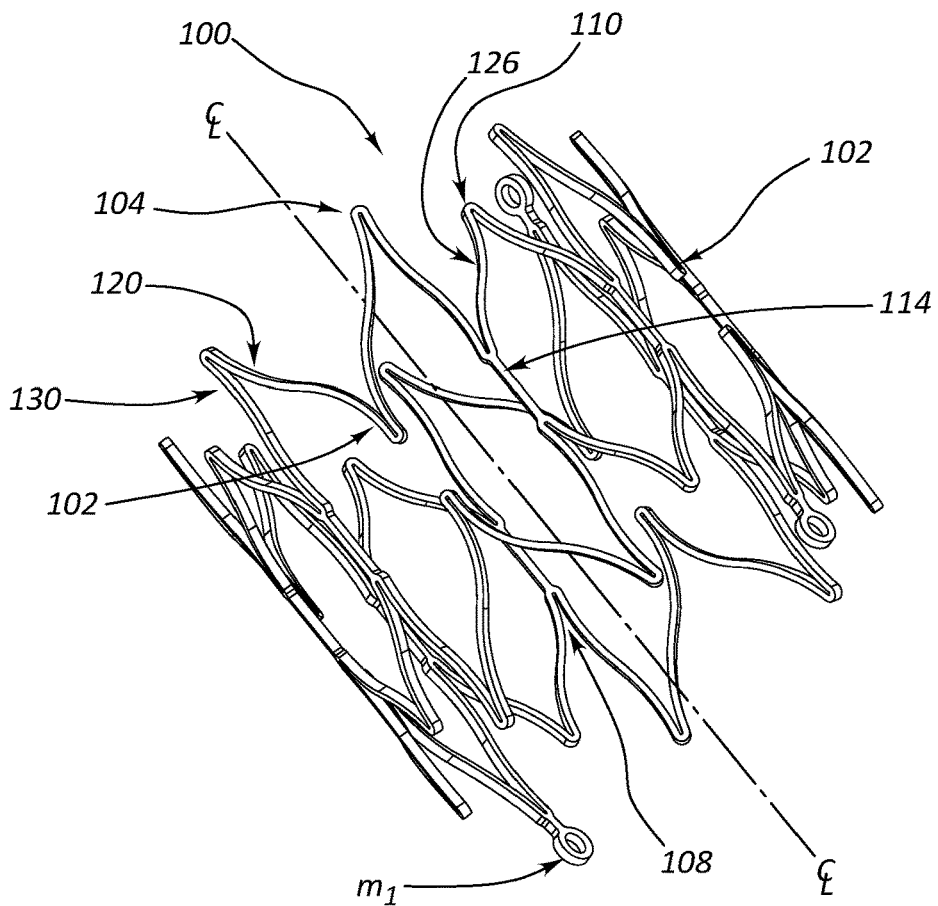
FIG. 1B is a stent, similar to that of FIG. 1A, but shown in a perspective view.
Figure 1C:
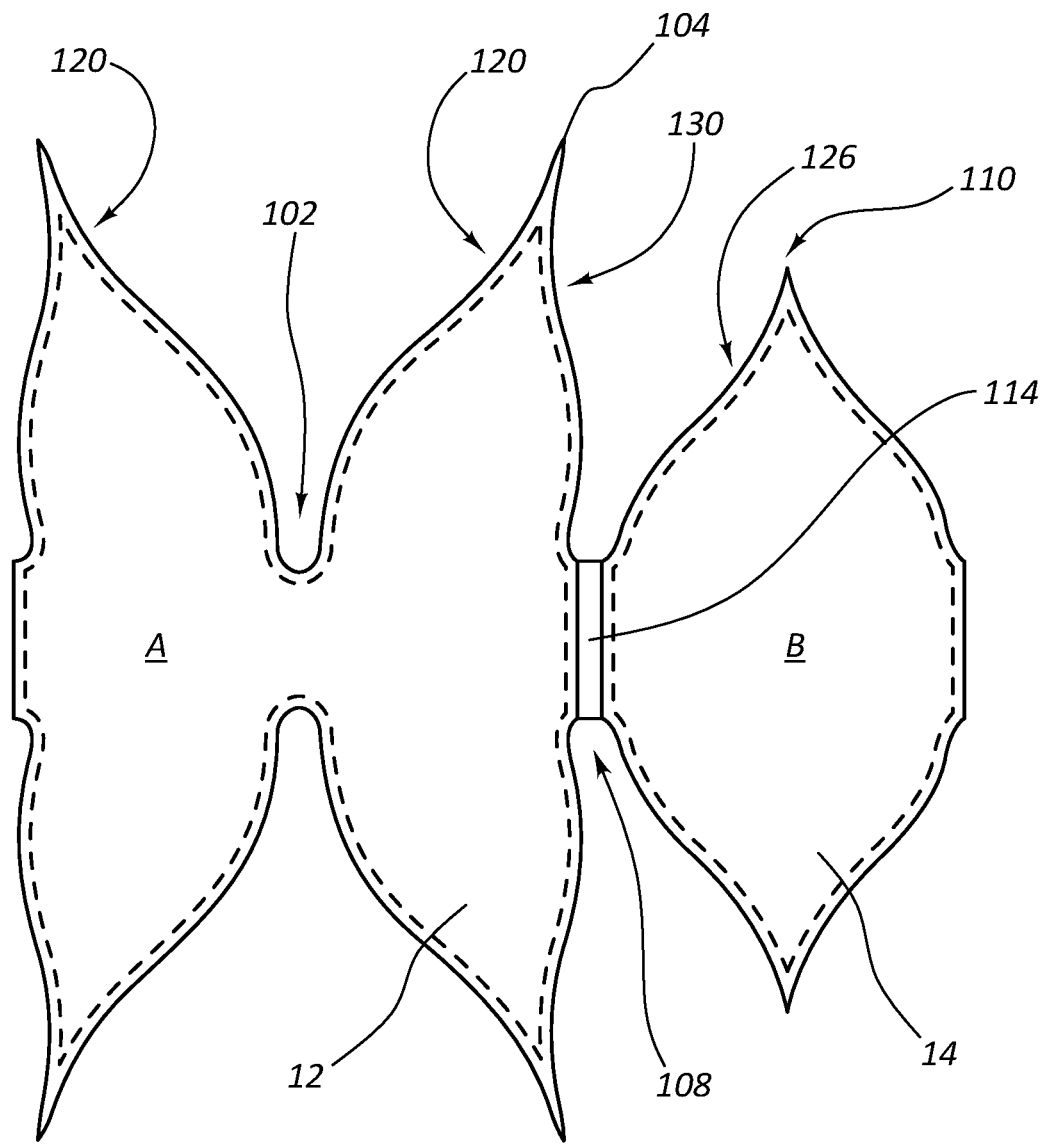
FIG. 1C shows two cells of the stent of FIG. 1A.

Referring to FIGS. 1A-C, stent 100 is shown, including a repeating pattern of two types of stent cells: stent cell A 12 and stent cell B 14 aligned along circumferences of circles perpendicular to longitudinal axis, ₵. The pattern can be arranged on one or more circumferences, depending on various stent dimensions including, e.g., stent length, stent cell length, connector length, etc. Stent cells 12 and 14 are formed from struts repeating along the circumferences. This pattern can have 3 to 8 repetitions. In some embodiments, this pattern repeats 4 times.

Beginning from the top left side of FIG. 1A, a repeating series of stent elements is shown extending from line 16. The struts form M-shaped and V-shaped sections. Generally, the M-shaped sections include a first c1-curved strut 130, followed by a v1-vertex 104, followed by a mirrored pair of c2-curved struts 120, and joined by a v2-vertex 102. Generally, the V-shaped stent elements include a mirrored pair of c3-curved struts 126, joined by a v3-vertex 110.

The struts forming M-shaped sections contribute to the perimeter around stent cell 12. The struts forming V-shaped sections contribute to the perimeter around stent cell 14.

Moving circumferentially around the stent ring, the M-shaped sections join to an adjacent inverted-V-shaped section through a first v4-vertex 108. The V-shaped section joins to an adjacent M-shaped section through a v4-vertex mirrored from that of the first v4-vertex 108, and so on.

V-shaped and M-shaped sections alternate around the ring until returning to the first M-shaped section. These alternating sections form a first, r1-ring. The shortest stent embodiments also comprise a second, r2-ring, which is a mirror image of the r1-ring. The two rings join through b1-bridges 114. The b1-bridges 114 join the rings by bridging corresponding v4-vertexes 108, one v4-vertex 108 lying in an r1-ring and another v4-vertex 108 lying in an adjacent r2-ring. An r1-ring and an r2-ring joined in this fashion yield an r3-ring. (The previous discussion neglects m1-markers 512.)

The stent ends comprise m1-markers 512 extending substantially longitudinally from one or more v1-vertexes 104.

Depending on the length of the stent embodiment, 1 to 100 instances of an r3-ring join to form the stent. Two adjacent instances of r3-rings connect through one or more b2-bridges 118 (FIG. 7), extending between adjacent v1-vertexes 104. A b2-bridge 118 joins r3-rings by bridging corresponding v4-vertexes 104 lying in adjacent r3-rings.

Some embodiments use an r1-ring comprising motif A. Stepping around r1-ring, motif A begins with a first c1-curved strut. Next, a v1-vertex connects a first c2-curved strut to the first c1-curved strut. A v2-vertex connects a second c2-curved strut to the first c2-curved strut. A v1-vertex connects a second c1-curved strut to the second c2-curved strut.

After that, a v4-vertex connects a first c3-curved strut to the second c1-curved strut. Next, a v3-vertex connects a second c3-curved strut to the first c3-curved strut. And a v2-vertex connects the first c1-curved strut to the second c3-curved strut. In some embodiments, any combination of curved struts c1, c2, and c3 can be substantially straight.

An alternative description of motif a follows. A v1-vertex connects a c1-curved strut to a c2-curved strut. A second v2-vertex connects two c2-curved struts. A third v3-vertex connects two, c3-curved struts. And a v4-vertex connects a c3-curved strut to a c1-curved strut.

In some embodiments having motif A, a c1-curved strut connects a v1-vertex and a v4-vertex. A c2-curved strut connects a v2-vertex to a v1-vertex. And a c3-curved strut connects a v3-vertex to a v4-vertex.

In some embodiments, the order of curved struts in motif A is c1, c2, c2, c1, c3, c3. And the order of vertexes in motif A is v1, v2, v1, v4, v3, v4. This does not take into account m1-markers.

Motif A can be repeated based on the desired circumference of the r1-ring; one or more repetitions of motif A exist in r1-ring, and one or more repetitions of motif A exist in r2-ring. In some embodiments, r1-ring comprises 4 instances of motif A.

FIG. 1C depicts cell 12 and cell 14. Alternatively, the stent pattern can be described as comprising two motifs x and y. Motif x comprises cell 12, which resembles a butterfly. Motif y comprises cell 14, which resembles an ellipsoid pinched on the ends of the major axis. Butterfly motif x alternates with ellipsoid motif y around r3-ring. For longer stents, r3-ring repeats one or more times. Adjacent rings, r3, join wing-tip-to-wing-tip through v4-vertexes.

Similarly, FIG. 1B depicts a perspective view of stent 100 in an expanded configuration. Stent 100 comprises two crown-shaped moieties that are mirror images of each other with the mirror plane perpendicular to stent 100's longitudinal axis. This is a crown-bottom-to-crown-bottom arrangement. Stent 100 comprises three types of curved struts 120, 126, 130 joined by four types of vertexes 104, 102, 108, 110.

The crown shapes connect to each other, having b1-bridge 114 connecting vertex 108 on one crown to its mirror image on the other crown.

The crown-shaped moieties comprise various curved-strut-vertex-curved-strut parts: strut 120, vertex 102, strut 120; strut 120, vertex 104, strut 130; strut 130, vertex 108, strut 126; strut 126, vertex 110, strut 126; strut 126, vertex 108, strut 130; and strut 130, vertex 104, strut 120. In some embodiments, this pattern repeats.

Neglecting m1-markers 512, stent 100 has a mirror plane perpendicular to the longitudinal axis, longitudinal mirror planes bisecting the v2-vertexes 102, longitudinal mirror planes bisecting the v3-vertexes 110, and a 4-fold longitudinal axis of rotation.

The following definition of strut length is used. A "strut length" is the length of a strut from a center of the radius of curvature of the vertex at one end of the strut to another center of the radius of curvature of the vertex at the other end of the strut. "c1" represents the strut length of a c1-curved strut; "c2" represents the strut length of a c2-curved strut; "c3" represents the strut length of a c3-curved strut; "b1" represents the strut length of a b1-bridge; "b2" represents the strut length of a b2-bridge.

In some embodiments, c1/b2=2.3-3.1; c2/b2=2.7-3.5; c3/b2=1.8-2.6; b1/b2=1.1-1.9; c1/b2=2.5-2.9; c2/b2=2.9-3.3; c3/b2=2.0-2.4; b1/b2=1.3-1.7; c1/b2=2.6-2.8; c2/b2=3.0-3.3.1; c3/b2=2.1-2.3; b1/b2=1.4-1.6.

A vertex angle is the smallest angle at a strut intersection. "v1" represents the angle of a v1-vertex; "v2" represents the angle of a v2-vertex; "v3" represents the angle of a v3-vertex; "v4" represents the angle of a v4-vertex.

In some embodiments, a v1-vertex occurs at the intersection of two struts, a v2-vertex occurs at the intersection two struts, a v3-vertex occurs at the intersection of two struts, a v4-vertex occurs at the intersection of two struts and a bridge; or any combination of these. Sometimes, a v1-vertex occurs at the intersection of two struts and a bridge.

In some embodiments v1 ranges from about 21-41, 26-36, or 30-32 degrees. In some embodiments v2 ranges from about 48-68, 53-63, or 57-59 degrees. In some embodiments v3 ranges from about 57-77, 62-72, or 66-68 degrees. In some embodiments v4 ranges from about 29-49, 34-44, or 28-40 degrees.

Figure 7A:
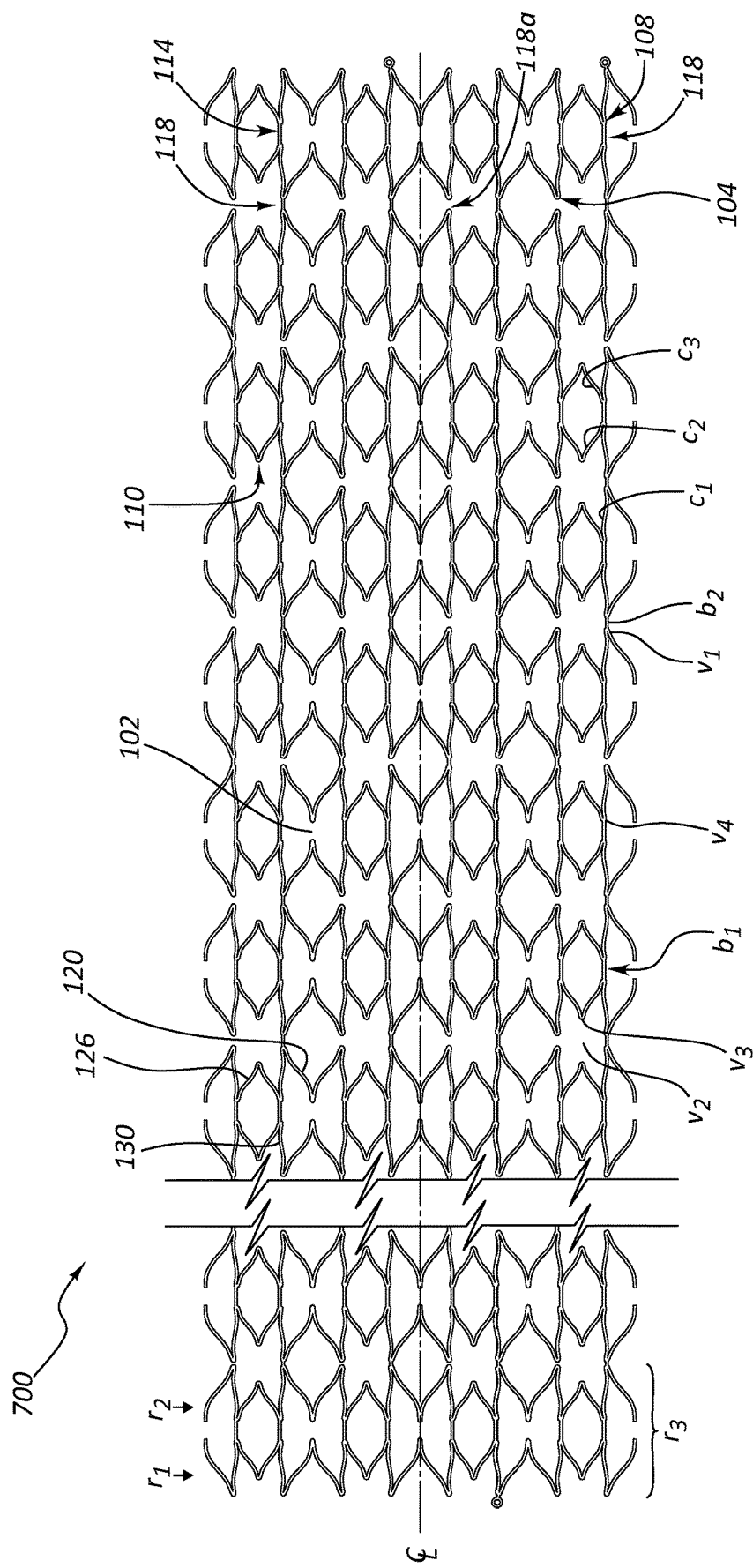
FIG. 7A is a laid out view of a longer stent embodiment.

FIG. 7A depicts a longer stent embodiment. In the figure, stent 700 has been cut and rolled flat. Longer versions of stent 100 comprise two or more bottom-to-bottom pairs or r3-rings, as described above. One bottom-to-bottom pair connects to an adjacent bottom-to-bottom pair through crown-top-to-crown-top b2-bridges 118 extending between a vertex 104 and its mirror-image counterpart. In some embodiments not all of vertexes 104 connect to their mirror-image counterparts. FIG. 7A also depicts b2-unbridged gap 118a between corresponding vertexes 104.

In some embodiments, every other vertex 104 attaches to its mirror image counterpart on an adjacent ring. In some embodiments, less than 90, 80, 70, 60, 50, 40, 30, 20, 10 percent of vertexes 104 connect to their mirror image counterparts. In some embodiments, smaller percentages of vertex 104 connections favor more flexible stents all other things being equal.

Figure 7B:
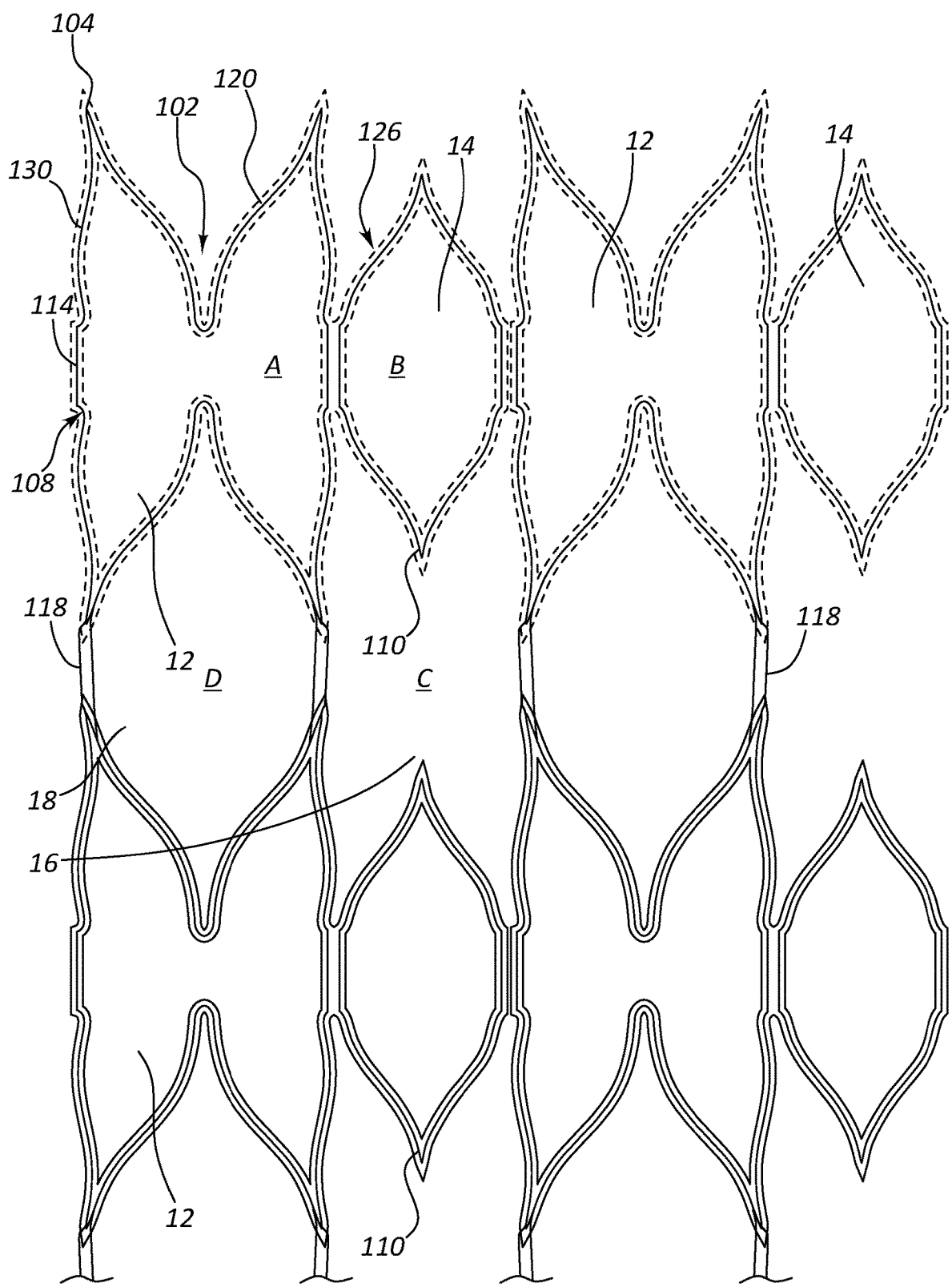
FIG. 7B is a view of stent cell from the stent of FIG. 7A.

Alternatively, as shown in FIG. 7B, stent 700 comprises four types of stent cells: stent cell a 12, stent cell B 14, stent cell C 16, and stent cell D 18. Cells 12 and 16 are butterfly shaped, but not equivalent. Cells 14 and 18 have the shape of an ellipse pinched at both ends of the major axis, but are not equivalent Stent 700 comprises a ring perpendicular to the longitudinal axis that comprises alternating cells 12 and 14. In some embodiments, this ring has 4-8 pairs of alternating cells 12 and 14. The stent comprises another ring perpendicular to the longitudinal axis and fused with the first ring that comprises alternating cell 16 and cell 18. In some embodiments, this ring has 4-6 pairs of alternating cells 16 and 18. Depending upon the desired stent length, more or fewer pairs of alternating rings are lined up in particular embodiments.

Cell 12 comprises two bridges 114, four struts 130, four struts 120, two vertexes 102, four vertexes 104, and four vertexes 108. These components are arranged in a butterfly shape. Taking these components in groups, cell 12 comprises: strut 130, vertex 104, strut 120; strut 120, vertex 102, stent 120; strut 120, vertex 104, strut 130; strut 130, vertex 108, bridge 114; bridge 114, vertex 108, strut 130; strut 130, vertex 104, strut 120; strut 120, vertex 102, strut 120; strut 120, vertex 104, strut 130; strut 130, vertex 108, bridge 114; and bridge 114, vertex 108, strut 130.

Cell 14 comprises two bridges 114, four struts 126, four vertexes 108, and two vertexes 110 arranged in a pinched-ellipsoid shape. Taking the components in groups, Cell 14 comprises: strut 126, vertex 110, strut 126; strut 126, vertex 108, bridge 114; bridge 114, vertex 108, strut 126; strut 126, vertex 110, strut 126; strut 126, vertex 108, bridge 114; and bridge 114, vertex 108, strut 126.

Cells 16 and 18 will be described as being completely bridged. But various embodiments exist having fewer than the total number of possible bridges.

Cell 16 comprises two bridges 118, four struts 126, four struts 130, four vertexes 104, two vertexes 110, and four vertexes 108, arranged in a butterfly shape.

Taking the components in groups, cell 16 comprises: strut 130, vertex 108, strut 126; strut 126, vertex 110, strut 126; strut 126, vertex 108, strut 130; strut 130, vertex 104, bridge 118; bridge 118, vertex 104, strut 130; strut 130, vertex 108, strut 126; strut 126, vertex 110, strut 126; strut 126, vertex 108, strut 130; strut 130, vertex 104, bridge 118; and bridge 118, vertex 104, strut 130.

Cell 18 has two bridges 118, four struts 126, two vertexes 102, and four vertexes 104 arranged in a pinched-ellipsoid shape. Taking these components in groups, cell 18 comprises: strut 120, vertex 102, strut 120; strut 120, vertex 104, bridge 118; bridge 118, vertex 104, strut 120; strut 120, vertex 102, strut 120; strut 120 vertex 104, bridge 118; and bridge 118, vertex 104, strut 120.

Returning to FIGS. 1A and 1B, the stents comprise substantially straight regions. One such region has the following sequence: strut 130, vertex 108, bridge 114, vertex 108, and strut 130. "Substantially straight," in some embodiments, means as straight as the elements of the sequence joined together as in FIG. 1A. In these or other embodiments, "substantially straight" regions comprise struts with a total distance, d. In some embodiments, "Substantially straight" means that the total deviation from linear is less than 10, 9, 8, 7, 6, 5, 4, 3, or 2 times d. Straight regions contribute to the stent's ability to resist foreshortening.

Returning to stent 700 of FIG. 7A, stent 700 has substantially straight regions substantially the same as stent 100. These straight regions join to other, similar, straight regions by bridges 118, in some embodiments. Since the number of bridges 118 is sometimes variable based on the desired stiffness of the stent, the length of joined, substantially straight regions varies. In some embodiments, the total length of the joined region exceeds 10, 20, 30, 40, 50, 60, 70, 80, 90, or 99 percent of the total length of the stent.

Described in another way, the substantially straight regions have struts, vertexes, and bridges in a sequence of strut, vertex, type-I bridge, vertex, strut, vertex, type-II bridge, vertex, strut, vertex, type-I bridge, vertex, strut.

In some embodiments, the substantially straight regions cause the stents to exhibit no foreshortening or to exhibit less foreshortening than stents with similar lengths exhibit upon expansion. In some embodiments, the total length of a substantially straight region is 6 mm.

Figure 2:
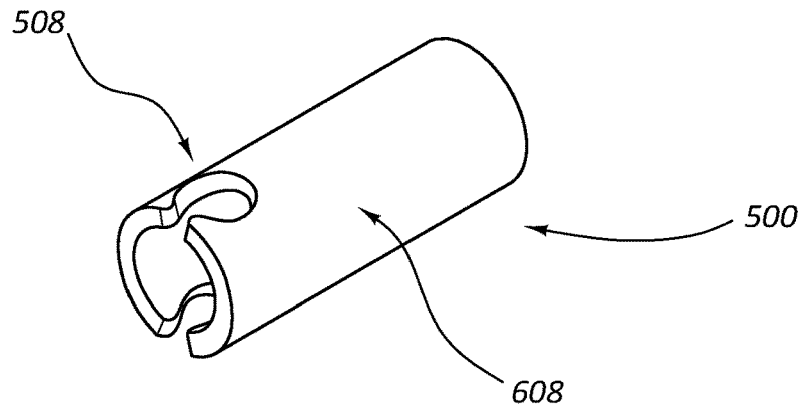
FIG. 2 shows an embodiment of a stent anchor.

FIG. 2 depicts a perspective view of stent holder 500 and receivers 508 formed from tube 608. Stent anchor 500 has a tubular structure and comprises any one or any combination of metal, ceramic, polymer, and glass. Stent holder 500 has an outer diameter similar to that of stent 100 when stent 100 is in its un-expanded configuration. When stent 100 assumes its expanded configuration, its diameter is greater than stent holder 500's diameter. Outer sheath 606 restrains stent 100.

Figure 3A:
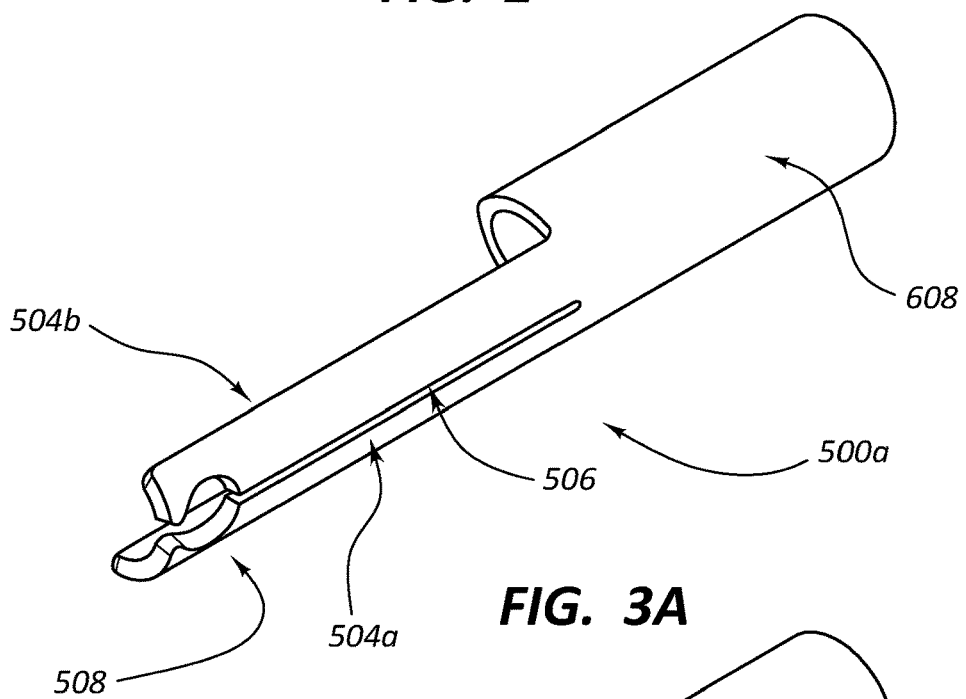
FIG. 3A shows a locked arrangement of a stent-anchor embodiment comprising fingers.

FIG. 3A depicts a perspective view of stent anchor 500a. Stent anchor 500a has a tubular structure and comprises any one or any combination of metal, ceramic, polymer, and glass. The stent anchor comprises one or more fingers 504a and 504b, which in this embodiment are formed by cutting tube 608 creating slits 506. Two or more adjacent fingers 504 comprise cut outs that align to form receiver 508, which is designed to interact with stent 100 (or stent 700). In some embodiments, receiver 508 holds the stent. In some embodiments receiver 508 serves as a locking mechanism; FIG. 3A depicts stent anchor 500a in the locked position.

Figure 3B:
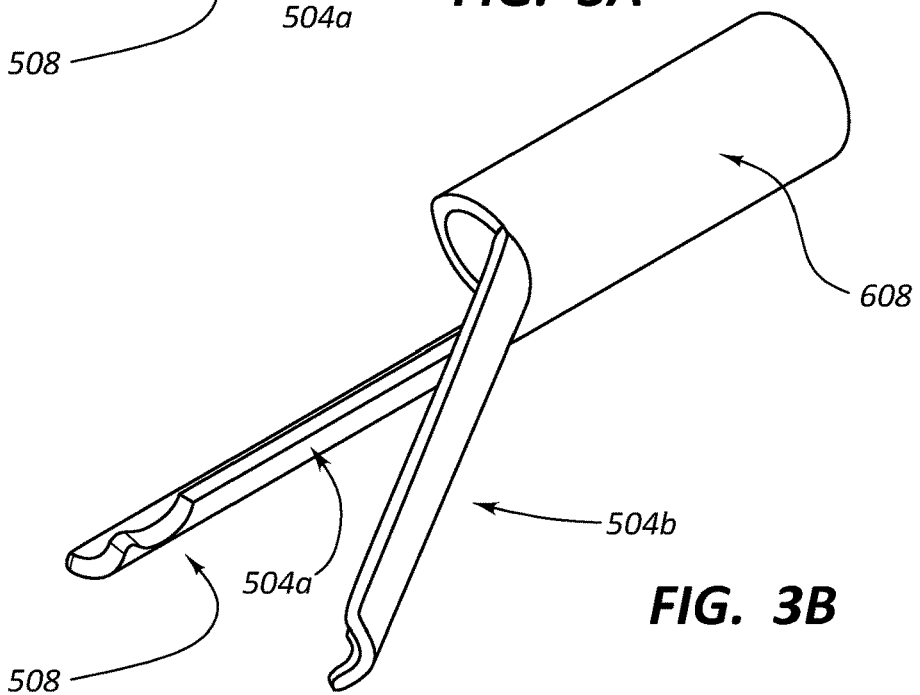
FIG. 3B shows an unlocked arrangement of the stent-anchor embodiment of FIG. 3A.

FIG. 3B depicts stent anchor 500a in the unlocked position. In this embodiment, finger 504a is substantially fixed and finger 504b is movable. In some embodiments, during the manufacture of stent anchor 500a, finger 504b is bent or biased such that finger 504b has a relaxed position as shown in FIG. 3B. This position operates as the unlocked position because the cutouts in fingers 504a and 504b do not align to create receiver 508 when the anchor is in this position.

But in some embodiments, fingers 504a and 504b are both bent or biased inwardly or outwardly.

Stent anchor 500a has an outer diameter that is substantially the same as the inner diameter of outer sheath 606 (depicted in FIG. 6B). That is, stent anchor 500a fits inside of and touches the inner surface of outer sheath 606. Likewise, due to its self-expanding nature, stent 100 touches the inner surface of outer sheath 606.

Outer sheath 606 restrains stent anchor 500a similarly to the way it restrains stent 100. Outer sheath 606 also restrains fingers 504a and 504b. When mounted on the delivery system, fingers 504a and 504b holding them in the locked position.

Figure 4A:
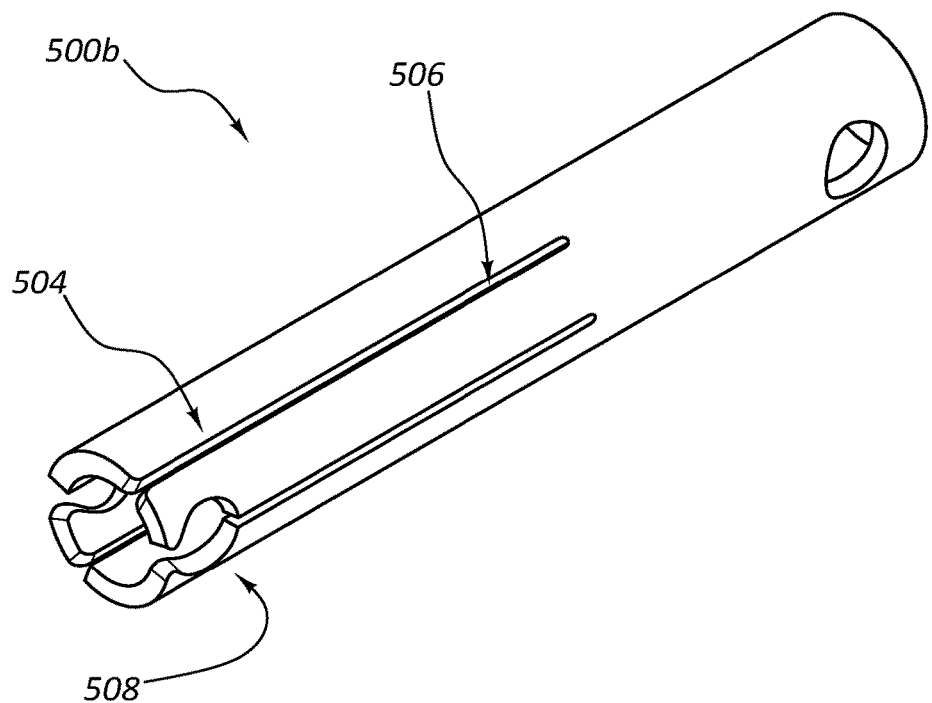
FIG. 4A is a perspective view of another stent anchor embodiment comprising fingers.

FIG. 4A depicts a perspective view of another embodiment of stent anchor 500b.

Figure 4B:
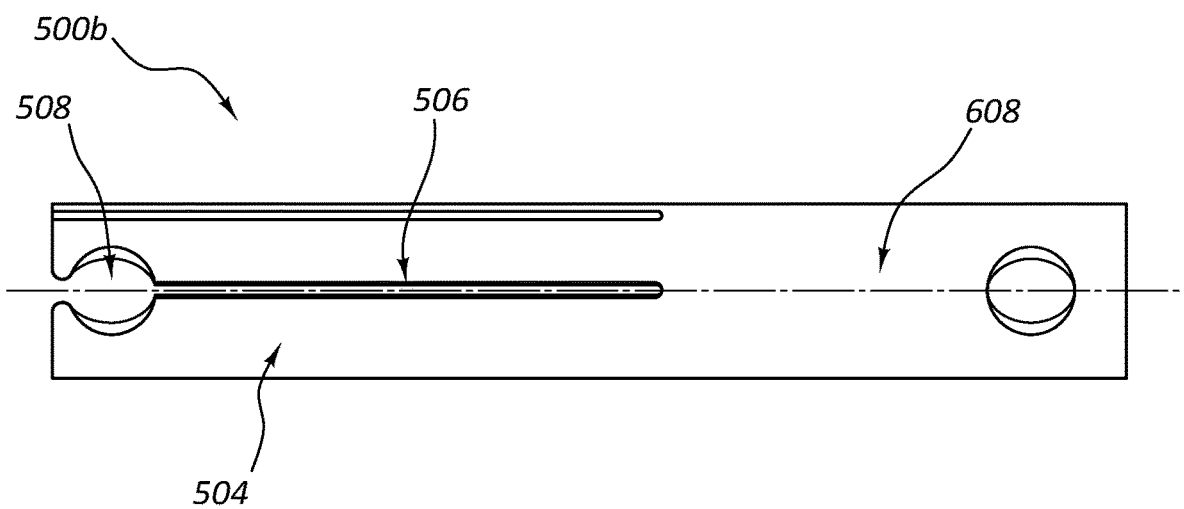
FIG. 4B is a side-view of the stent-anchor embodiment of FIG. 4A.

Stent anchor 500b comprises four fingers 504 cut from tube 608 with receiver 508 formed in fingers 504. FIG. 4B is a side view of the stent anchor of FIG. 4A. Stent anchor 500b has an outer diameter that is substantially the same as the inner diameter of outer sheath 606. That is, stent anchor 500b fits inside of and touches the inner surface of outer sheath 606. Likewise, due to its self-expanding nature, stent 100 touches the inner surface of outer sheath 606. Since markers 512 lie inside of receiver 508, stent 100 is held in place. Stent 100 is held in place by the capture of marker 512 inside of receiver 508 (as shown in FIG. 5).

Additionally, similar to those of FIGS. 3A and 3B, stent anchor 500b has at least two configurations. FIG. 4A illustrates stent anchor 500b in a locked configuration. The embodiments in these figures can also have one or more bent or biased fingers.

Outer sheath 606 restrains stent anchor 500b similarly to the way it restrains stent 100 and stent anchor 500a. The unlocked configuration comprises at least one of fingers 504 extends radially inward or outward because finger 504 is bent or biased that way.

Figure 5:
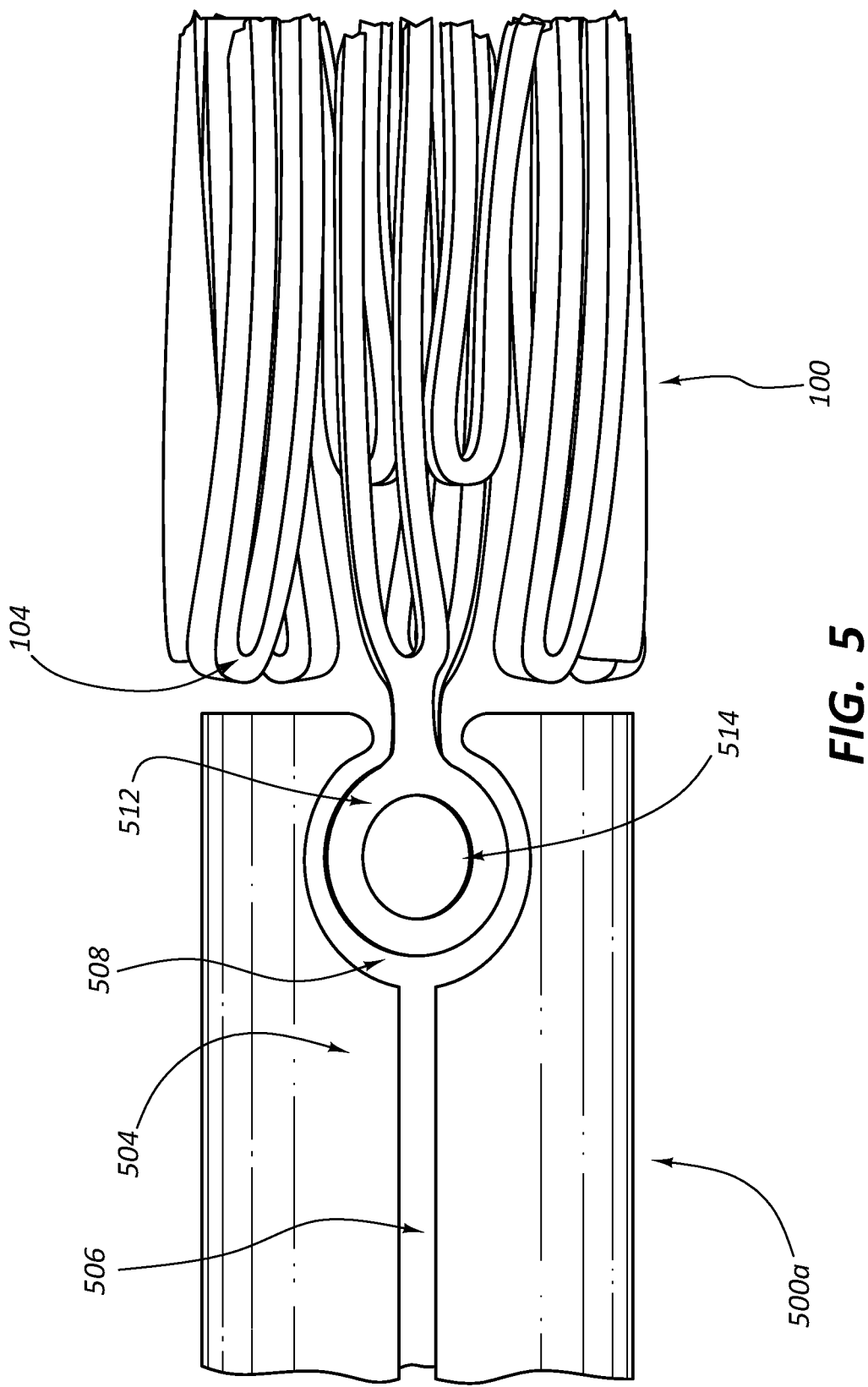
FIG. 5 is a view of a stent anchor interacting with a crimped stent.

FIG. 5 depicts stent anchor 500a engaged with stent 100. As discussed above, stent 100 can have two arrangements: compressed and expanded. FIG. 5 depicts stent 100 in the compressed arrangement. Stent 100 comprises at least one vertex 104, as described above. (FIG. 1B depicts stent 100 in the expanded state.)

Stent 100 engages stent anchor 500a through the interaction between receiver 508 and marker 512. In some embodiments, marker 512 comprises radiopaque insert 514, which provides the stent with increased visibility under fluoroscopy.

FIG. 6A depicts a stent delivery system 600 having distal end 601 and inner catheter 610. Stent bed 602 is proximal of distal tip 604. Stent anchor 500a is proximal of stent bed 602, coaxially around inner catheter 610. Stent anchor 500a comprises one or more fingers 504. These fingers are shaped to create stent receiver 508 situated at the distal end of stent anchor 500a.

FIG. 6B depicts a stent delivery system 600 similar to that of FIG. 6A, but additionally including outer sheath 606 and compressed stent 100.

Stent delivery system 600 comprises a distal end 601 which comprises stent bed 602 located in a distal region of distal end 601. Stent bed 602 has a smaller diameter than adjacent portions of the stent delivery system in some embodiments.

Stent 100 is clamped or crimped onto stent delivery system 600 at stent bed 602. In some embodiments, the inner surface of stent 100 interacts with stent bed 602.

An outer sheath 606 extends over stent 100 constraining stent 100 in a radially compressed deliver configuration that has a small enough diameter to fit coaxially into outer sheath 606.

In some self-expanding embodiments, the expansion halts when stent 100 expands out to the inner surface of outer sheath 606. The outer sheath can retract or move proximally relative to stent 100 and stent anchor 500a to a retracted position in which distal-most end 607 of retractable sheath 606 lies proximally of proximal most end 603 of stent 100.

Delivery system 600 also comprises distal tip 604 which aids delivery system 600 in traveling through the vasculature and protects stent 100 during this transit. While stent 100 is mounted on stent bed 602, stent anchor 500a holds stent 100 in place, resisting proximal or distal motion, because receiver 508 captures marker 512.

The FIG. 6 embodiments depict receiver 508 and marker 512 as circular. But any pair of cooperative or complementary shapes is useful for these components.

In operation, a physician threads stent delivery system 600 through a patient's vasculature until it reaches the intended delivery site. This insertion is typically monitored by fluoroscopy with insert 514 providing a more intense image because it has higher radiopacity than surrounding substances. The physician initiates delivery of stent 100 by beginning to retract outer sheath 606 using any one of a number of suitable retraction mechanisms. As outer sheath 606 uncovers stent 100, the uncovered portion begins to automatically expand. As stent 100 expands, the capture of marker 512 in receiver 508 prevents any tendency towards distal movement. Once distal-most end 607 is proximal of marker 512, marker 512 releases from receiver 508. Releasing marker 512 releases stent 100.

In embodiments with stent anchor 500 as shown in FIG. 2, stent 100 releases from stent anchor 500 by expansion. Proximal retraction of outer sheath 606 uncovers all of stent 100 and allows it to expand. But expansion of the region of stent 100 that contains captured marker 512 does not occur until stent 100 is mostly uncovered, i.e. retraction completes. Then, stent 100 finishes moving radially outward, which causes marker 512 to also move radially outward. Once the inner diameter of stent 100 exceeds the outer diameter of stent anchor 500, marker 512 clears receiver 508 and marker 512 is no longer held in place.

And retraction frees stent 100, allowing it to radially expand from the delivery configuration to the delivered or expanded configuration.

In embodiments with stent anchor 500a or 500b as shown in FIGS. 3A, 3B, 4A, and 4B. Stent 100 releases from stent anchor 500a or 500b by expansion, as described above for stent anchor 500. Retraction of outer sheath 600 allows stent 100 to expand into its expanded state. The expansion of the region of stent 100 that contains the captured marker does not occur until that portion becomes uncovered during retraction. But in these embodiments, retraction does not complete until fingers 504a and 504b are uncovered.

At that time, finger 504b springs back to its unlocked position. So, in these embodiments, stent 100 is released by marker 512 moving out of receiver 508, as with stent anchor 500, and by finger 504b moving such that receiver 508 no longer exists. Having two release mechanisms provides redundancy in case one of the mechanisms does not fully release stent 100. Some embodiments of stent anchor 500b release in this way, as well.

The stents or any portion of the stents can be bare, coated, covered, encapsulated, or bio-resorbable.

Bio-active agents can be added to the stent (e.g., either by a coating or via a carrier medium such as resorbable polymers) for delivery to the host vessel or duct. The bio-active agents can also be used to coat the entire stent. A coating can include one or more non-genetic therapeutic agents, genetic materials and cells and combinations thereof as well as other polymeric coatings. Non-genetic therapeutic agents include anti-thrombogenic agents such as heparin, heparin derivatives, urokinase, and PPack (dextrophenylalanine pro line arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/antimiotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, an RGD pep-tide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms. Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor alpha and beta, platelet-derived endothelial growth factor, platelet-derived growth factor, tumor necrosis factor alpha, hepatocyte growth 15 factor and insulin like growth factor, cell cycle inhibitors including CD inhibitors, thymidine kinase ("TK") and other agents useful for interfering with cell proliferation the family of bone morphogenic proteins ("BMPs"), BMP-2, BMP-3, BMP-4, BMP-5, BMP-6 (Vgr-1), BMP-7 (OP-1), BMP-8, BMP-9, BMP-10, BMP-1, BMP-12, BMP-13, BMP-14, BMP-15, and BMP-16. Desirable BMP's are any of BMP-2, BMP-3, BMP-4, BMP-5, BMP-6 and BMP-7. These dimeric proteins can be provided as homodimers, heterodimers, or combinations thereof, alone or together with other molecules. 25 Alternatively or, in addition, molecules capable of inducing an upstream or downstream effect of a BMP can be provided. Such molecules include any of the "hedgehog" proteins, or the DNAs encoding them. Cells can be of human origin (autologous or allogeneic) or from an animal source (xenogeneic), genetically engineered if desired to deliver proteins of interest at the deployment site. The cells can be provided in a delivery media. The delivery media can be formulated as needed to maintain cell function and viability. 35 Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropy-45-lene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL® fibrin, collagen and derivatives thereof, polysaccharides such as celluloses, starches, dextrans, alginates and derivatives, hyaluronic acid, squalene emulsions. 55 Polyacrylic acid, available as HYDRO PLUS® (from Boston Scientific Corporation of Natick, Mass.), and described in U.S. Pat. No. 5,091,205, the disclosure of which is hereby incorporated herein by reference, is particularly desirable. Even more desirable is a copolymer of poly lactic acid and polycaprolactone.

What is claimed is:

1. A stent delivery system, comprising:
an inner tubular member;
a stent disposed over a distal section of the inner tubular member, the stent including an architecture having only two rows of connected struts, the two rows of connected struts comprising a first row of struts connected by a first plurality of vertexes and a second row of struts connected by a second plurality of vertexes, the second row of struts attached to the first row of struts via a plurality of bridge struts, wherein the second row of struts are a mirror image of the first row of struts, and wherein:
each of the first row of struts and the second row of struts include first struts having a first length, and second struts having a second length longer than the first length,
the first row of struts and the second row of struts are arranged in a pattern of two first struts followed by four second struts,
each of the first struts are connected together at an end vertex,
each of the first struts are connected to a second strut at a first middle vertex, and
each first middle vertex is attached to one of the plurality of bridge struts;
a locking member positioned over the inner tubular member proximal of the stent, wherein a portion of the stent is positioned in the locking member, the locking member comprising:
a tubular proximal section; and
a plurality of fingers extending distally from the tubular proximal section, the plurality of fingers including a first finger and a second finger, the plurality of fingers having a locked configuration with each of the first finger and the second finger parallel to a longitudinal axis of the stent delivery system, and an unlocked configuration with one or both of the first finger and the second finger forming an angle with respect to the longitudinal axis of the stent delivery system; and
an outer tubular member covering the stent and the locking member in a delivery configuration, the outer tubular member designed to move proximally with respect to the stent and the locking member to release the stent at a desired location.

2. The stent delivery system according to claim 1, further comprising a distal tip coupled to a distal end of the inner tubular member, distal of the stent, the distal tip having a diameter larger than a diameter of the inner tubular member.

3. The stent delivery system according to claim 1, wherein the first finger is adjacent to the second finger, wherein a distal end of the first finger includes a first portion of a shaped recess, and wherein a distal end of the second finger includes a second portion of the shaped recess.

4. The stent delivery system according to claim 3, wherein the shaped recess is configured to receive the portion of the stent.

5. The stent delivery system according to claim 4, wherein the portion of the stent positioned in the shaped recess includes a radiopaque marker.

6. The stent delivery system according to claim 5, wherein the shaped recess and the portion of the stent have a circular shape.

7. The stent delivery system according to claim 1, wherein the plurality of fingers together form a tubular shape, wherein adjacent fingers of the plurality of fingers include complementary recesses that together correspond to the portion of the stent.

8. The stent delivery system according to claim 1, wherein each of the first row of struts and the second row of struts include at least one radiopaque member extending from at least one of the second struts.

9. The stent delivery system according to claim 8, wherein the at least one radiopaque member extends from at least one of the second struts connected to one of the first struts.

10. The stent delivery system according to claim 1, wherein four consecutive second struts form an M-shape.

11. The stent delivery system according to claim 10, wherein the second struts are curved.

12. The stent delivery system according to claim 1, wherein the second struts not connected to a first strut are connected together at a second middle vertex, wherein the second middle vertex is not connected to one of the plurality of bridge struts.

13. The stent delivery system according to claim 1, wherein a series of closed cells are formed between the first row of struts and the second row of struts.

14. The stent delivery system according to claim 13, wherein the series of closed cells are formed into a first motif and a second motif different from the first motif, wherein the first motif and the second motif alternate circumferentially about the stent.

* * * * *